United States Patent

Homsy

[11] 4,052,754
[45] Oct. 11, 1977

[54] IMPLANTABLE STRUCTURE

[76] Inventor: Charles A. Homsy, 11526 Raintree Circle, Houston, Tex. 77024

[21] Appl. No.: 705,334

[22] Filed: July 14, 1976

Related U.S. Application Data

[63] Continuation-in-part of Ser. No. 604,624, Aug. 14, 1975, abandoned.

[51] Int. Cl.² .......... A61F 1/24; A61F 1/18; A61B 19/00; A61N 1/04
[52] U.S. Cl. .......... 3/1.9; 128/1 R; 128/82.1; 128/418; 128/419 F; 128/419 P
[58] Field of Search .......... 3/1, 1.9–1.91, 3/1.4; 128/1 R, 334 R, 334 C, 82.1, 419 F, 419 P, 418, 404

[56] References Cited

U.S. PATENT DOCUMENTS

| 3,176,316 | 4/1965 | Bodell | 3/1 |
|---|---|---|---|
| 3,196,462 | 7/1965 | Robinson | 3/1 |
| 3,473,170 | 10/1969 | Haase et al. | 3/1 |
| 3,680,542 | 8/1972 | Cimber | 128/1 R |
| 3,687,129 | 8/1972 | Nuwayser | 128/1 R |
| 3,797,047 | 3/1974 | Pillet | 3/1 |
| 3,828,764 | 8/1974 | Jones | 128/1 R |
| 3,931,648 | 1/1976 | Shea | 3/1.9 |

FOREIGN PATENT DOCUMENTS

| 2,347,213 | 3/1974 | Germany | 3/1.9 |

*Primary Examiner*—Ronald L. Frinks
*Attorney, Agent, or Firm*—Vinson & Elkins

[57] ABSTRACT

A structure for in vivo implantation which includes an elongate section terminating in one end in an enlarged portion and being at least partially of a biocompatible porous material having characteristics of promoting ingrowth of tissue. The structure is adapted to be implanted in place of at least a portion of the bony chain of the middle ear, to serve as a plug for a tube, or to serve as an implant electrode. The same structure including a means for closing the pores of the intermediate portion of such structure may be used in place of all or a portion of the bony chain between the ear drum and the vestibule.

16 Claims, 12 Drawing Figures

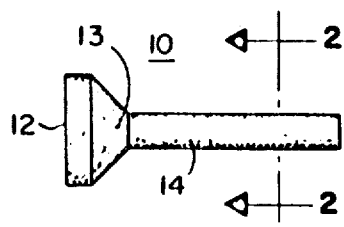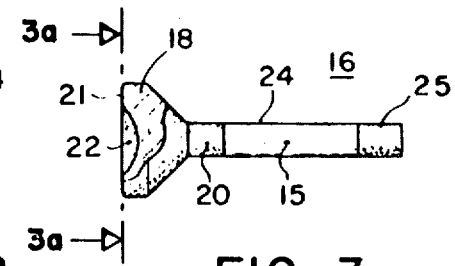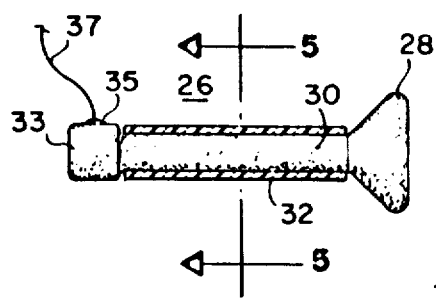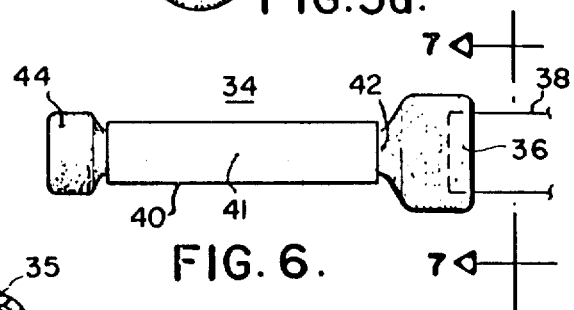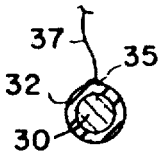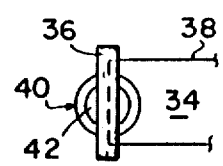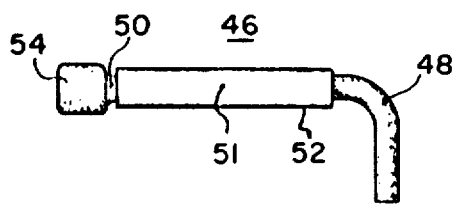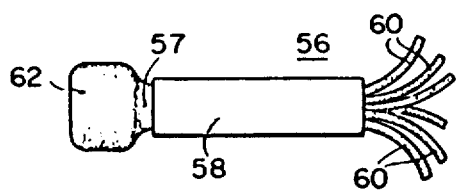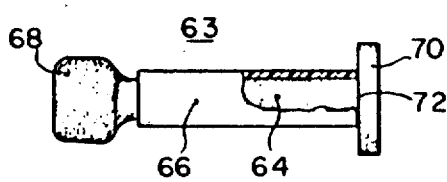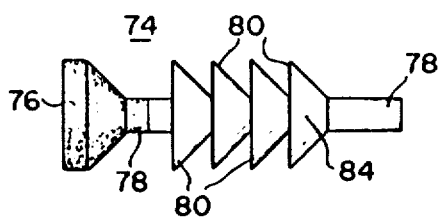

4,052,754

IMPLANTABLE STRUCTURE

CROSS-REFERENCE AND RELATED APPLICATIONS

The present application is a continuation-in-part of my prior copending application Ser. No. 604,624, filed Aug. 14, 1975, now abandoned.

BACKGROUND OF THE INVENTION

One of the reasons for deafness is the failure of the bony chain, i.e., the hammer, the anvil and the stirrup to transmit the vibrations of the ear drum to the inner ear. Efforts have been made to repair the elements of the bony chain and to substitute components therefor. With the substitution of components, one difficulty encountered is the securing of such components in the desired position. One example of a solution is my prior copending application, Ser. No. 425,105, filed Dec. 17, 1973, now U.S. Pat. No. 3,909,852, which provides the structure with a biocompatible columella and a biocompatible porous pad secured to at least one of the ends of the columella. The present invention is an improvement thereon in that the biocompatible porous material may be used to form the columella and extend beyond each end to provide the ingrowth material for the securing of the implant in the desired position.

This offers an improved structure for the transmission of sound vibrations in the ear since the improved structure of the present invention has a continuity of material throughout its length.

During recent years many efforts have been made to provide a simple, reversible birth control method which did not have any possible side effects. The birth control pill has been used but with certain individuals the pill has undesirable side effects. A positive method of sterilization for women has been to cut and close the fallopian tubes. Such method is not reversible so that it should not be used if the woman may at a later date desire to have children.

Also, certain physiological processes, such as fracture healing, heart beat pacing, pain modulation, etc., can be controllably modified by passing electric current into a selected tissue of a living organism. A common means of passing electric current is to insert a noble metal electrode into the organism. Using such metal electrodes, it was found that the current density distribution to the selected tissue cannot be easily controlled.

SUMMARY

The present invention relates to an improved structure suitable for an in vivo implantation, such as, a substitute for the bony chain or parts thereof in the ear or to close the uterine end a fallopian tube or to provide for the passing of an electric current into a selected tissue of a living organism.

An object of the present invention is to provide an improved structure for in vivo implantation which is totally biocompatible and is designed to promote the ingrowth of tissue to secure the implant in its desired position.

An object of the present invention is to provide an improved structure for implanting in the ear and substitution for the bony chain and having improved sound transmitting properties.

A still further object of the present invention is to provide an improved vibration transmitting implant for the ear which utilizes growth promoting porous materials and avoids difficulties of tissue growth around the central or column portion of the implant.

Still another object is to provide an improved structure for in vivo implantation which closes the opening of a fallopian tube into the uterus by ingrowth of tissue therein.

In its most general configuration, the improved structure of the present invention for in vivo implantation comprises a porous element defining a pad and a stem extending from the central portion of the pad. The pad and the stem are biocompatible and promote the ingrowth of living tissue. For most applications, the stem can have transverse dimensions between 0.25 and 3 millimeters, and the pad's largest dimension can be between 0.5 and 8 millimeters.

The improved structure is adapted to be implanted in place of at least a portion of the bony chain of the middle ear. The stem is made sufficiently long to approximate the dimensions of the bony chain which it replaces, and, preferably, the surface pores of the center portion of the stem are closed.

Also, it is preferred that the surface pores of nearly the entire stem be closed when the structure is used as a plug for the fallopian tubes opening into the uterus. The pad has a dimension to allow sufficient tissue ingrowth to secure the structure in its implanted position. Added securing by ridges along the stem can be provided to resist movement of the structure from its implanted position.

A fluoroethylene propylene tube can be heat shrunk onto the stem for closing its surface pores. The end of the stem which extends beyond the tube can have one or more leaves, or the end can be enlarged in one dimension to form a flat, bulbous end portion with sufficient flexibility to bend at a substantially right angle to the longitudinal axis of the stem. A wire can be connected to an end of the stem. Also, a disc of porous ingrowth-promoting material can be bonded to one end of the stem.

In general, the pad will be frusto-conical in shape with its larger end facing outwardly. When the pad defines a shallow recess for receiving a portion of the bony chain therein, the improved structure can serve as a stapes replacement.

The porous material of the element forming the structure can have the property of conducting electric current. Therefore, such structure can serve as an improved in vivo electrode, which is totally biocompatible. By virtue of having a substantial tissue ingrowth within its pores, such electrode offers a relatively-large contact area for current distribution between the electrode and the ingrown and thereto contiguous tissue. In this manner, better control of electric current distribution between the electrode and the contiguous tissue can be achieved.

BRIEF DESCRIPTION OF THE DRAWINGS

These and other objects and advantages are hereinafter set forth and explained with respect to the drawings wherein:

FIG. 1 is a side view of one shape of improved structure of the present invention.

FIG. 2 is an end view of the structure shown in FIG. 1.

FIG. 3 is a sectional view of the improved structure used for replacement of the stapes of the ear.

FIG. 3a is an end view taken along line 3a—3a on FIG. 3.

FIG. 4 is a longitudinal sectional view of another form of implantable structure of the present invention.

FIG. 5 is a sectional view of the implantable structure shown in FIG. 4 taken along lines 5—5.

FIG. 6 is a side view of another form of improved structure of the present invention.

FIG. 7 is an end view of the implantable structure shown in FIG. 6.

FIG. 8 is a side view of another form of improved structure for use as a bony chain replacement in the ear.

FIG. 9 is a side elevation view of another form of implantable structure of the present invention.

FIG. 10 is a side view of another form of implantable structure of the present invention.

FIG. 11 is a side view of still another modified form of implantable structure of the present invention.

DESCRIPTION OF THE PREFERRED EMBODIMENTS

The implantable structure shown in FIG. 1 is the preferred form in that it may be used as a tube plug or as a bony chain substitute. The structure 10 includes the pad 12 which may be of any shape but is preferred to be generally frusto-conical and has the stem 14 integral with and extending from the central portion of pad 12. For most application, the pad's largest dimension is between 0.5 and 8 millimeters. Stem 14 has transverse dimensions between 0.25 and 3 millimeters. At least a substantial portion of the exterior of pad 12 and the end of stem 14 away from pad 12 are porous and of a material designed to promote the ingrowth of tissue therein. Only the exterior of pad 12 need be porous when the structure is used as a tube plug. In those applications in which the structure 10 is to be used as a substitute for at least a portion of the bony chain of the ear it is preferred that stem 14 have its outer surface either compressed or otherwise treated to have limited porosity to avoid the ingrowth of tissue around its exterior.

The ingrowth material for the improved structures of the present invention is preferred to be a material which is porous and which readily promotes the ingrowth of living tissues into the pores and voids within the material. A typical example of the preferred form of the material is disclosed in my copending application, Ser. No. 515,443, filed Oct. 17, 1974, now U.S. Pat. No. 3,992,725, which is a continuation-in-part of application Ser. No. 416,641, filed Nov. 16, 1973, now abandoned which was a continuation of application Ser. No. 145,497 filed May 20, 1971, now abandoned. In such application a porous material of carbon fibers bonded by polytetrafluoroethylene is disclosed as the preferred growth promoting material. An added advantage of using the ingrowth promoting material of the above-mentioned application as an electrode is that the tissue growing therein will not restrict or adversely affect the electrode's connection because the ingrowing and ingrown tissues are protected by the flexibility of such material. For example, the instance of electrode use in conjunction with pulsatile cardiac tissue would preserve mechanical and electrical coupling between the electrode and tissue in the presence of physiological motion of adjacent tissue. Other suitable growth promoting materials are disclosed in such application and the disclosure is herein incorporated by reference. The present invention also has application to other biocompatible growth promoting materials which may be implanted and cause living tissues to ingrow therein.

The structure 16 illustrated in FIG. 3 is a sectional view of a stapes replacement for implant in the ear. Such structure includes the frusto-conical pad 18 and the stem 20. The structure 16 is the same as structure 10 except that the outer end of pad 18 defines a concave recess 22 and the exterior of the portion of the stem 20 adjoining pad 18 has its external pores at least partially closed as indicated by the shade area 24. The structure 10 could be cut from a piece of the ingrowth material and does not have any means for closing its external pores. The structure 16 may be developed from a cylindrical block of the ingrowth material and the tapered portion of pad 18 and all of the stem 20 except for its outer end are compressed to the shape illustrated to obtain the surface 24 with the pores closed or sufficiently restricted to prevent growth of tissue through such surface 24. The outer end of stem 20 may be trimmed to size as shown. Preferably it should not exceed the diameter of the recess of the vestibule but be a close fit therein. The recess 22 is shaped to receive the bony chain. An unexpected advantage of structure 16 formed by compression along the central portion 15 of the stem 20 is that such portion exhibits substantial mechanical hysteresis. This mechanical characteristic can be advantageous in allowing the surgeon to more precisely shape the geometry of structure 16 relative to the middle ear architecture.

The closing of the pores of the materials as shown in area 24 in FIG. 3 may be accomplished by pressure, pressure and heat or any other suitable means to assure that the surface porosity is reduced sufficiently so that tissue growth does not pass through the surface. In addition to surface treatment, mechanical means such as shrink sleeves or pore-occluding coatings of medical grade materials, such as silicone rubber, polymeric dispersions, etc., can also be used as the pore-closing means, as hereinafter described.

In structure 26 shown in FIGS. 4 and 5 the pad 28 is frusto-conical in shape and has the stem 30 integral therewith and extending therefrom. The stem 30 includes a means for closing the pores around its exterior. The closing means shown is the tubular sleeve 32 which surrounds the exterior of stem 30 except for the outer end thereof. The tubular sleeve 32 is a biocompatible plastic tube which has been shrunk into its position surrounding stem 30 as shown. The sleeve 32 and all materials used for in vivo implants are to be completely biocompatible so that they do not cause any reaction of the tissues when implanted. An example of suitable material for sleeve 32 is a fluorinated ethylene propylene tube which may be shrunk onto the stem 30 at temperatures within the range from 400° to 450° F without damaging the ingrowth material of stem 30 and pad 28. These sleeves are characterized as being good electrical insulators.

The structure 34 shown in FIGS. 6 and 7 is similar to the structure 26 of FIG. 4 but has an enlarged flat end 36 into which the wire 38 is fixed. The sleeve 40 is shrunk about the central portion of stem 42 with end 36 and end 44 extending thereform as shown. The structure 34 can be used as a stapes replacement or as an electrode, as will be hereinafter set forth.

The structure 46 shown in FIG. 8 is substantially the same as structure 34 but would be longer and is designed to be a replacement for the entire bony chain of the ear. The structure 46 includes the enlarged flat end 48 integral with the stem 50 about which the sleeve 52 is shrunk leaving end 48 and end 54 extending therefrom. End 48 is sufficiently thin to be flexible so that it may be positioned at an angle to stem 50 and rest flat on the ear drum. With this shape a large area of ingrowth material is exposed to the ear drum to assure positive fixation by ingrowth.

In the shrink fitting of the closure means sleeves such as the sleeve 18 on the element 16 such shrink fitting is done by any process well known in the art. For example the shrink fitting may be accomplished by heating air and passing the heated air over the expanded tubular sleeve which has been placed in the surrounding relation to the central part of the element 16 for a relatively short period of time such as, for example, a few seconds. In such case, sufficient heat should be provided to exceed the setting temperature and the material remembers its original size and returns thereto, squeezing the central portion of the stems as shown. The shrink sleeves are of a material which prevents living tissue from growing and attaching thereto. It also should be selected so that it does not cause appreciable dampening of the vibration transmission from the ear drum to the oval window of the inner ear.

A modified form of the implant is shown in FIG. 9 wherein the element 56 has been provided with a shrink fit sleeve 58. However, one end of the element projecting from the tube 22 has been separated into a plurality of leaves 60 which leaves may make an improved connection to the oval window or the ear drum than a simple end pad. The other end 62 of the element 56 is relatively flexible as described in relation to end 48 in FIG. 8 and may be folded to lay flat against the ear drum or oval window.

The implant shown in FIG. 10 is another modified form that includes elongate element 64 having a shrink fit sleeve 66 over the central portion thereof with only one end 68 of the elongate portion 64 projecting from the end of the sleeve. The other end of the sleeve 66 is covered by the pad 70 which includes the biocompatible porous material which is adapted to promote ingrowth of tissue thereon and a film 72, such as fluorinated ethylene propylene, which bonds the pad 70 to the end of the sleeve 66. Structure 63 can be made, if desired, without an end 68 projecting outwardly of sleeve 66.

A modified structure 74 is shown in FIG. 11 designed to be used as a fallopian tube closure plug. It includes a pad 76 and a stem 78 provided with external ridges 80 facing toward pad 76. Ridges 80 are preferably formed in such a manner that their external surfaces have their pores closed, as represented by the shaded area 84, so as to prevent the ingrowth of tissue. Such ridges 80 can be formed by compressing or molding of stem 78 so long as the external pores on the ridges 80 are sufficiently closed to prevent tissue ingrowth. When structure 74 is used as a plug for a tube, ridges 80 will provide sufficient resistance to the traveling contractions of the tube so that the plug will not be displaced from its desired position before the ingrowth of tissue has progressed sufficiently within the pad 76 to secure the structure in place. Hence, ridges 80 serve to impede the displacement of the plug within the tube.

The structures of the present invention for implantation in the ear may be described as being an elongate porous element with pore closing means over a substantial portion of the central part of the element with the ends of the element extending beyond the pore closing means.

The porous material as described in the British Pat. No. 1,390,445 is a fairly good electric conductor and, therefore, electric current density would be distributed over the entire structure of this invention and would flow into the ingrown tissue. Therefore, each of the structures shown in FIGS. 1–11 can also serve as an implant current-carrying electrode. In its simplest form shown in FIG. 6, wire 38 would carry an electric current to the tissues in the pores of structure 34, while sleeve 40 would serve to insulate the tissues adjoining the sleeve, thereby providing selective current density distribution.

In a modified form, a wire 37 can be attached to end 33 of stem 30 (FIG. 4) with the aid of a thin biocompatible layer or film 35 of a rare metal such as gold or platinum. Wire 37 can also be mechanically secured to end 33. Similarly, each of the shown embodiments of the implant structure can be adapted to serve as an implant electrode.

As previously mentioned the closing means may be provided by the compression and sealing of such central portion of the stem responsive to pressure or pressure and heat so that the exterior of the stem along its central proportion prevents attachment of tissue thereto and outgrowth of tissue therefrom. With respect to the closure means any suitable material which is totally biocompatible and which would occlude or close the porosity to prevent ingrowth of tissue therein or outgrowth of tissue there would be suitable.

From the foregoing it will be appreciated that the present invention provides an improved structure for in vivo implantation, such as a fallopian tube plug, or in place of all or part of the bony chain between the ear drum and the inner ear, or as an implant electrode with selective current density distribution; the structure is relatively simple to make and involves the use of a porous biocompatible material and relatively simple manufacturing procedures.

What is claimed is:

1. A structure for in vivo implantation, comprising
an elongate biocompatible, porous element, said porous element having at least a portion of its length compressed so that the surface pores along said portion are closed,
one projecting end of said element being enlarged and having open pores throughout to allow tissue ingrowth therein,
said porous element having the characteristics of promoting ingrowth of living tissue therein when implanted.

2. A structure according to claim 1, wherein said element includes a stem and a pad, said pad being the enlarged end of said element, said stem extending from the central portion of said pad.

3. A structure according to claim 2 wherein
said stem has a transverse dimension between 0.25 and 3 millimeters, and
said pad's largest dimension is between 0.5 and 8 millimeters.

4. A structure according to claim 2 wherein
said structure is adapted to be implanted in place of at least a portion of the bony chain of the middle ear, and
said stem is sufficiently long to approximate the dimension of the bony chain which it replaces.

5. A structure according to claim 2 wherein
said structure is adapted to be implanted into the end of a fallopian tube opening into the uterus, and said stem is of sufficient dimension to prevent its displacement from its initial implanted position until tissue ingrowth has progressed sufficiently to secure such structure in its implanted position.

6. A structure according to claim 5 wherein the exterior of said stem is formed as ridges to resist movement from its implanted position.

7. A structure according to claim 1, including means for closing said closed surface pores.

8. A structure according to claim 7 wherein both ends of said element project beyond said pore closing means.

9. A structure according to claim 7 wherein said pore closing means is a fluoroethylene propylene tube which is heat shrunk onto said element.

10. A structure according to claim 1 wherein the end of said element extending beyond said closed surface pores is divided into a plurality of leaves.

11. A structure according to claim 1 wherein the end of said element extending beyond said closed surface pores is enlarged in one dimension to form a flat bulbous end portion with sufficient flexibility to bend at substantially a right angle to said element.

12. A structure according to claim 1 including a wire connected to and extending from said projecting end of said element.

13. A structure according to claim 1 including a pad of porous ingrowth promoting material, and means for bonding said pad to the end of said element opposite the end projecting beyond said closed surface pores.

14. A structure according to claim 1 wherein the enlarged end of said element is frusto-conical in shape with the larger end thereof facing outwardly.

15. A structure according to claim 14 wherein said structure is for a stapes replacement and said outer end includes a shallow recess for receiving a portion of the bony chain therein when implanted.

16. A structure according to claim 1 wherein said structure is of material having the property of conducting electric current, and including means connected to said material for feeding electric current to said structure when it is implanted as an electrode.

* * * * *